United States Patent [19]

Hashimoto et al.

[11] 3,983,241

[45] Sept. 28, 1976

[54] IMIDAZOLE DERIVATIVES

[75] Inventors: Sho Hashimoto, Odawara; Akira Nakada, Hiratsuka; Saburo Kano; Susumu Takahashi, both of Odawara, all of Japan

[73] Assignee: Ni, Tokyo, Japan

[22] Filed: July 28, 1975

[21] Appl. No.: 599,664

[30] Foreign Application Priority Data

Aug. 9, 1974   Japan.................................. 49-90775

[52] U.S. Cl.................................. 424/273; 260/309
[51] Int. Cl.².................................... C07D 233/90
[58] Field of Search....................... 260/309; 424/273

[56] References Cited
UNITED STATES PATENTS 3,770,764   11/1973   Webster............................. 260/309

FOREIGN PATENTS OR APPLICATIONS 1,459,782   10/1966   France............................. 260/309.2

OTHER PUBLICATIONS

Noller Chemistry of Organic Compounds 2nd ed. p. 244 Philadelphia, Saunders, 1957.

Primary Examiner—Natalie Trousof
Attorney, Agent, or Firm—George B. Oujevolk

[57] ABSTRACT

This invention is directed to compositions and methods employing, as an active fungicidal ingredient, at least one compound of the formula:

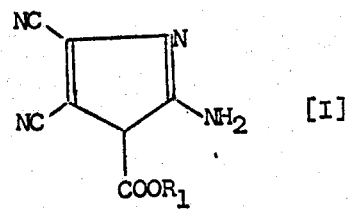

wherein $R_1$ is selected from the group consisting of straight or branched chain alkyl, lower alkenyl, lower alkynyl, lower alkoxyethl, lower haloalkyl and lower cycloalkyl.

Especially preferred for use because of their fungicidal effectiveness are:

2-amino-1-n-butoxycarbonyl-4,5-dicyanoimidazole and
2-amino-4,5-dicyano-1-n-pentyloxycarbonylimidazole.

15 Claims, No Drawings

IMIDAZOLE DERIVATIVES

DETAILED DESCRIPTION OF THE INVENTION:

This invention relates to novel compounds of imidazole derivatives, to a process for the preparation thereof and their used as fungicide.

More particularly, this invention is directed to compositions and methods employing, as an active fungicidal ingredient, at least one compound of the formula:

[I]

wherein $R_1$ is selected from the group consisting of straight or branched chain alkyl, lower alkenyl, lower alkynyl, lower alkoxyethyl, lower haloalkyl and lower cycloalkyl.

Especially preferred for use because of their fungicidal effectiveness are:

2-amino-1-n-butoxycarbonyl-4,5-dicyanoimidazole and
2-amino-4,5-dicyano-1-n-pentyloxycarbonylimidazole.

The compound of this invention can be prepared by the following equation:

[II] + [III] → [I]

wherein $R_1$ is as previously defined.

As a practical method of the above reaction, 2-amino-4,5-dicyanoimidazole [II] is dissolved in an organic solvent together with a condensing agent in amounts equimolar with it and chloroformic ester [III] is added dropwise to the mixture at room temperature. As an organic solvent, acetone, dioxane, benzene, acetonitrile, dimethylsulfoxide, dimethylformamide, preferably acetone, are used.

For condensing agents, sodium carbonate, potassium carbonate, sodium bicarbonate, potassium bicarbonate, sodium hydroxide, potassium hydroxide and triethylamine can be used. Then, the temperature of resulting mixture is raised to 40°- 100°C and maintained at its temperature during 0.5 to 1 hour, but the reaction proceeds at a room temperature. When the reaction mixture is poured into cold water after finishing the reaction, the crystal of the crude product separates out and the crude product can be purified by recrystallization.

Another method of the preparation is illustrated by the following equation:

[II] + [IV] → [I]

wherein $R_1$ is as previously defined.

The above reaction can be conducted in an inert solvent such as pyridine, alkylpyridine, quinoline, alkylquinoline or isoquinoline and the reaction temperature is from room temperature to 100°C.

In order that the invention may be better understood, the following examples are given:

EXAMPLE 1.

2-amino-1-ethoxycarbonyl-4,5-dicyanoimidazole 1.33 g of 2-amino-4,5-dicyanoimidazole was dissolved in 10 ml of suspension of aceton containing 0.7 g of anhydrous potassium carbonate and then 1.1 g of ethyl chloroformate was added dropwise to the solution at a room temperature.

The resulting solution was refluxed during 30 minutes, and white crystal separated out when the reaction mixture was poured into ice-water. After recrystallizing the crude product from methanol, 1.6 g of purified compound having a melting point of 195° to 197°C was obtained as needles. (Yield rate: 78% )

EXAMPLE 2.

2-amino-1-n-butoxycarbonyl-4,5-dicyanoimidazole 2 g of 2-amino-4,5-dicyanoimidazole was dissolved in 20 ml of suspension of acetone containing 1.3 g of sodium bicarbonate and then 2.1 g of n-butyl chloroformate was added dropwise to said solution at a room temperature. The resulting solution was refluxed during 30 minutes, and white crystal was separated out when the rection mixture was poured into ice-water. After recrystallizing the crude product from methanol, 2.7 g of the purified compound having a melting point of 170° to 172°C was obtained as needles (Yield rate: 77%).

EXAMPLE 3.

2-amino-4,5-dicyano-1-n-pentyloxycarbonylimidazole 2 g of 2-amino-4,5-dicyanoimidazole was dissolved in 20 ml of acetonitrile, 1.6 g of triethylamine was added to said solution and further 2.3 g of n-amyl chloroformate was added dropwise to it at a room temperature. The resulting solution was refluxed during 30 minutes, and white crystal was separated out when the reaction mixture was poured into ice-water. After recrystallizing the crude product from methanol, 3.1 g of the purified compound having a melting point of 166 to 169°C was obtained as needles (Yield rate: 83%).

EXAMPLE 4.

1-allyloxycarbonyl-2-amino-4,5-dicyanoimidazole 2 g of 2-amino-4,5-dicyanoimidazole and 2 g of allyl chloroformate were added to 20 ml of acetone and further 3 ml of water solution containing 20% of sodium hydroxide was added dropwise to it under stirring at a temperature of 15° to 20°C. After the resulting solution was stirred during an hour at a room temperature, it was poured into ice-water and thereby white crystal was separated out.

After recrystallizing the crude product from methanol, 2.3 g of the purified compound having a melting point of 186 to 188°C with decomposition was obtained as needles (Yield rate: 70%).

EXAMPLE 5.

2-amino-1-ethoxycarbonyl-4,5-dicyanoimidazole 2 g of 2-amino-4,5-dicyanoimidazole was dissolved in 20 ml of pyridine 2.5 g of diethyl pyrocarbonate was added dropwise to it and then it was stirred during two hours at a room temperature.

When the reaction mixture was poured into ice-water, white crystals were separated out. After recrystallizing the crude product from methanol, 2.1 g of the purified compound having a melting point of 195° to 197°C was obtained (Yield rate: 68%).

In addition to the above mentioned compounds described in the preceding example, some typical compounds of the present invention are listed in Table 1.

As mentioned previously, it has been found that the compound of this invention posses outstanding fungicidal activity.

The paragraphs which follow described in more detail the utility of this invention.

The compounds of the invention control a wide variety of fingus diseases of foliage, fruit, stems and roots of growing plants without damage to the host.

The many fungi against which the compounds of this invention are active may be represented by, but is not intended to be limited to, the following:
  alternaria leaf spot (*Alternaria mali*),
  black spot (*Alternaria kikuchiana*),
  late blight (*Phytophthora capsici*),
  crown rust (*Puccinia coronate corda*),
  helminthosporium leaf spot (*Cochliobolus miyakeanus*),
  downy mildew (*Pseudoperonospora cubensis*)
and particularly effective against alternaria leaf spot Table 1

| Compound No. | $-R_1$ | Physical Constant | Elemental Analysis (%) C | H | N |
|---|---|---|---|---|---|
| 1 | $-CH_3$ | m.p. 190–191°C | 43.82* | 2.89 | 36.48 |
|   |   |   | (43.89)** | (2.62) | (36.65) |
| 2 | $-C_2H_5$ | m.p. 195–197°C | 46.50 | 3.68 | 33.94 |
|   |   |   | (46.83) | (3.41) | (34.15) |
| 3 | $-C_3H_7{}^i$ | m.p. 170–173°C | 49.55 | 4.27 | 32.25 |
|   |   |   | (49.31) | (4.11) | (31.96) |
| 4 | $-C_4H_9{}^n$ | m.p. 170–172°C | 51.20 | 4.93 | 29.73 |
|   |   |   | (51.50) | (4.72) | (30.04) |
| 5 | $-C_4H_9{}^i$ | m.p. 181–183°C | 51.72 | 5.03 | 30.18 |
|   |   |   | (51.50) | (4.72) | (30.04) |
| 6 | $-C_5H_{11}{}^n$ | m.p. 166–169°C | 53.12 | 5.46 | 28.40 |
|   |   |   | (53.44) | (52.6) | (28.34) |
| 7 | $-C_5H_{11}{}^i$ | m.p. 181–184°C | 53.20 | 5.43 | 28.14 |
|   |   |   | (53.44) | (5.26) | (28.34) |
| 8 | $-C_6H_{13}{}^n$ | m.p. 163–165°C | 55.05 | 6.06 | 26.57 |
|   |   |   | (55.17) | (5.75) | (26.82) |
| 9 | $-C_7H_{15}{}^n$ | m.p. 162–164°C | 56.58 | 6.03 | 25.22 |
|   |   |   | (56.73) | (6.18) | (25.45) |
| 10 | $-C_8H_{17}{}^n$ | m.. 194–196°C | 58.42 | 6.64 | 24.20 |
|   |   |   | (58.13) | (6.57) | (24.23) |
| 11 | $-CH_2CH=CH_2$ | m.p. 186–188°C (with decomposition) | 49.45 | 3.28 | 32.24 |
|   |   |   | (49.77) | (3.33) | (32.36) |
| 12 | $-CH_2C \equiv CH$ | m.p. 201–203°C (with decomposition) | 49.91 | 2.42 | 32.32 |
|   |   |   | (50.23) | (2.33) | (32.56) |
| 13 | —⟨H⟩ | m.p. 178–181°C (with decomposition) | — | — | — |
| 14 | $-C_{12}H_{25}{}^n$ | m.p. 158–161°C | — | — | — |
| 15 | $-\underset{\underset{CH_3}{\mid}}{CH}-CH\underset{CH_3}{\overset{CH_3}{<}}$ | m.p. 147–149°C | — | — | — |
| 16 | $-CH_2CH=CHCH_3$ | m.p. 135–137°C | — | — | — |
| 17 | $-CH_2CHBrCHBrCH_3$ | m.p. 168–170°C | — | — | — |
| 18 | $-CH_2CH_2CH_2CH_2Cl$ | m.p. 159–161°C | — | — | — |
| 19 | $-CH_2CH_2OCH_3$ | m.p. 150–153°C | — | — | — |
| 20 | $-CH_2CH_2Cl$ | m.p. 165–168°C | — | — | — |
| 21 | $-CH_2CHClCH_2Cl$ | m.p. 169–172°C | — | — | — |

*Found
**Calculated

Hereinafter, the compounds of this invention are represented by compound No. of Table 1.

and black spot.

Further the compounds are used for seeds dressing against helminthosporium leaf spot.

It is another advantage that the compounds of the present invention have low toxicity for warm-blooded animals and fish.

The method of the present invention comprehends the employment of a liquid or solid composition containing one or more of the present compounds as an active component.

The compound can be used directly without mixing with suitable carriers. The active ingredient of this invention may be formulated by mixing with suitable carriers in a form generally used in pesticidal compositions such as wet table powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, xylene, cyclohexane, cyclohexanone, dimethylformamide, dimethylsulfoxide, alcohol, acetone, benzene and others are used. Sometimes surface active agent is added in order to give a homogeneous and stable formulation.

The concentrations of the active ingredients in the fungicidal composition of this invention vary according to type of formulation and they are, for example, used in a range of 5 – 80 weight percent, preferably 20 – 80 weight percent, in wettable powders, 5 – 70 weight percent, preferably 10 – 50 weight percent, in emulsifiable concentrates, and 0.5 – 20 weight percent, preferably 1 – 10 weight percent in dust formulations.

Incidentally, wettable powder or emulsifiable concentrate containing proper quantity of the active compound is suspended or emulsified in water and then sprayed to the foliages of the plants or to the soil around the cultivated plants. Furthermore, the compounds may be used as a mixture with other fungicides, insecticides, acaricides and herbicide.

Some examples in this invention are stated below. But the main compounds and the additives are not defined limitedly by these Examples.

EXAMPLE 6.

Wettable Powder

|  | Parts by weight |
|---|---|
| Compound No. 1 | 40 |
| Sodium alkylsulfonate | 7 |
| Diatomaceous earth | 53 |

These are mixed homogeneously and reduced to fine particles. Consequently, wettable powder containing 40% of the active ingredient is obtained. In practical use, it is diluted to a certain concentration with water and is sprayed as a suspension.

EXAMPLE 7.

Emulsifiable Concentrate

|  | Parts by weight |
|---|---|
| Compound No. 2 | 30 |
| Polyoxyethylenealkylarylether | 8 |
| Xylene | 42 |
| Dimethylformamide | 20 |

These are mixed and dissolved. Consequently, emulsifiable concentration containing 30% of the active ingredient is obtained. In practical use, it is diluted to certain concentration with water and then is sprayed as an emulsion.

EXAMPLE 8.

Dust Formulation

|  | Parts by weight |
|---|---|
| Compound No. 3 | 10 |
| Talc | 90 |

These are mixed homogeneously, reduced to fine particles. Consequently, dust formulation containing 10% of the active ingredient is obtained. In practical use, it is directly applied.

The superior fungicidal activity of compounds of this invention is clearly illustrated by the following tests.

Test 1.

Test for Control of Alternaria leaf spot

Apple leaves were cut off from the potted apple plant (variety: starking) and the detached leaves were immersed during 30 to 60 seconds into the diluted solution of a specified concentration of wettable powder containing test compound.

After air-drying, the leaves were inoculated with the spore suspension of *Alternaria mali* in the concentration of 200,000/ml and incubated in a wet chamber at 28°C.

One day after innoculation, an average number of lesions was examined and evaluation of percent disease control was calculated on the basis of number of lesions occuring on the untreated check.

The state of preventing against the germinating of spore on leaves was also observed through a microscope. The result was shown in Table 2.

Table 2

| Test Compound | Concentration of active ingredient (ppm) | Control Value (%) | State of inhibition of spore germination* |
|---|---|---|---|
| 4 | 250 | 100 | + |
|  | 125 | 100 | + |
|  | 63 | 90 | ± |
| 5 | 250 | 80 | ± |
|  | 125 | 75 | − |
|  | 63 | 75 | − |
| 6 | 250 | 100 | ± |
|  | 125 | 90 | − |
|  | 63 | 80 | − |
| 11 | 250 | 80 | ± |
|  | 125 | 40 | − |
|  | 63 | 30 | − |
| Captafol** | 800 | 100 | + |

Table 2-continued

| Test Compound | Concentration of active ingredient (ppm) | Control Value (%) | State of inhibition of spore germination* |
|---|---|---|---|
| | 400 | 100 | + |
| | 200 | 100 | + |
| | 100 | 80 | + |
| Untreated | — | 0 | — |

*degree for state of inhibiton of spore germination:
 —: normal germination
 ±: abnormal germination
 +: inhibition of spore germination
**cis-N[(1,1,2,2-tetrachloroethyl)thio]-4-cyclohexene-1,3-dicarboximide

Test 2.

Pot Test for Control of Alternaria leaf spot

The potted young apple plants (Star King) were sprayed, at a rate of 100 ml. per plant, with an aqueous suspension having a concentration of 500, 250 and 125 ppm of an active ingredient which suspension was prepared by diluting a wettable powder with water to a specified concentration. Young branches having about 7 to 8 leaves were cut off from each tree and leaves were also cut off from tree after allowing to stand for 1 day, 3 days and 7 days in green-house after the spraying of above suspension, and then inoculated with spore suspension of *Alternaria mali*, and held under the condition of incubation for 24 hours in a wet chamber. Then, average number of lesions per branch was counted and evaluation of percent disease control was calculated on the base of number of lesions occuring on the untreated check. The state of inhibition of the spore germination was also observed.

Table 3

| Test Compound | Concentration of active ingredient (ppm) | Control Value (%) Time between spraying and inoculation (days) | | | | |
|---|---|---|---|---|---|---|
| | | Detached branch | | | Leaf | |
| | | 1 | 3 | 7 | 1 | 7 |
| 4 | 500 | 95 | 100 | 100 | 80+ | 95+ |
| | 250 | 80 | 90 | 70 | 80± | 85+ |
| | 125 | 85 | 85 | 80 | 80± | 70± |
| 6 | 500 | 89 | 90 | 98 | 75± | 80~± |
| | 250 | 74 | 87 | 50 | 73— | 78± |
| | 125 | 81 | 81 | 66 | 70— | 63— |
| Polyoxnes* | 50 | 100 | 100 | 100 | 100+ | 100+ |
| Captafol** | 800 | 100 | 100 | 100 | 100+ | 100+ |
| Untreated | — | 0 | 0 | 0 | 0— | 0— |

*A series of antibiotic substances produced in culture solution of a Japanese *Streptomyces* species.
**cis-N-[(1,1,2,2-tetrachloroethyl)thio]-4-cyclohexene-1,3-dicarboximide.

Table 4

| Test compound | Concentration of active ingredient (ppm) | Control Value (%) |
|---|---|---|
| 1 | 500 | 100 |
| | 250 | 98 |
| | 125 | 71 |
| 2 | 500 | 100 |
| | 250 | 97 |
| | 125 | 95 |
| 3 | 500 | 91 |
| | 250 | 28 |
| 4 | 250 | 100 |
| | 125 | 100 |
| | 63 | 95 |
| 5 | 250 | 100 |
| | 125 | 100 |
| | 63 | 30 |
| 6 | 250 | 100 |
| | 125 | 100 |
| | 63 | 84 |
| 11 | 250 | 100 |
| | 125 | 100 |
| | 63 | 95 |
| Captan* | 250 | 100 |
| | 125 | 100 |
| | 63 | 100 |
| Untreated | — | 0 |

*cis-N-[(trichloromethyl)thio]-4-cyclohexene-1,3-dicarboximide

Test 3.

Test for Control of Late blight

Tomato leaves were cut off form the potted tomato (variety: Oogatafukuju) and the detached leaves were immersed during 30 to 60 seconds into the diluted solution of a specified concentration of wettable powder containing test compound. After air-drying, the leaves were inoculated with the zoospore suspension of late blight (*Phytophthora capsici*) in the concentration of 30,000/ml and incubated in a green-house at 28°C. 2 days after inoculation, the disease degree was examined and evaluation of percent disease control was calculated on the disease degree of untreated check. The results were shown in Table 4.

Test 4.

Test for Control of Late blight

Seeds of tomato (variety: Oogatafukuju) were planted in a pot and cultivated for 2 weeks in a greenhouse.

When cotyledons developed or leaves began to develop, 45 ml of an aqueous suspension prepared by diluting a wettable powder with water to a specified concentration was sprayed on the pot where 20 tomatoes seedlings were growing up. After the pot was placed in a green-house for 3 days, tomatoes were inoculated with the zoospore suspension of late blight (*Phytophthora*

*capsici*) in the concentration of (30,000/ml) and incubated in a wet chamber at 28°C.

Three days after inoculation, the disease degree was examined an evaluation of percent disease control was calculated on the base of the disease degree on the untreated check.

Each test was repeated three times for each concentration. The average results were shown in Table 5.

Table 5

| Test compound | Concentration of active ingredient (ppm) | Control Value (%) |
|---|---|---|
| 1 | 500 | 93.9 |
|   | 250 | 89.6 |
| 2 | 500 | 98.5 |
|   | 250 | 95.2 |
| 4 | 500 | 100 |
|   | 250 | 100 |
| 5 | 500 | 100 |
|   | 250 | 93.1 |
| 6 | 500 | 100 |
|   | 250 | 100 |
| 11 | 500 | 100 |
|    | 250 | 92.9 |
| Captan (50% wettable powder) | 250 | 100 |
|   | 125 | 98.2 |
| Untreated | — | 0 |

Test 5.

Pot test for Control of Late blight

A tomato seedling (height: 45 – 50 cm, leaves: 15 – 20) was grown in a pot.

60 ml of an aqueous suspension prepared by diluting a wettable powder with water to a specified concentration was sprayed on the two pot and these pots were allowed to stand in a green-house.

5 days after spraying, tomato seedlings were inoculated with the zoospore suspension of late blight and incubated in a wet chamber at 28°C.

Three days after inoculation, the disease degree was examined and evaluation of percent disease control was calculated on the base of the disease degree on the untreated check. The results were shown in Table 6.

Table 6

| Test compound | Concentration of active ingredient | Degree of disease* leaf | stem | Phytotoxicity |
|---|---|---|---|---|
| 2 | 500 | —~± | — | none |
| 4 | 500 | — | — | none |
| Captan | 250 | —~± | — | none |
| Untreated | — | ++~++++ | ±~++ | none |

*Degree of disease
leaf
—: healthy
±: disease below 5%
+: disease below 20%
++: disease below 40%
+++: disease below 60%
++++: disease beyond 60%
stem
—: healthy
±: disease of petiole
+: disease of stem
++: disease of middle of stem It is to be observed therefore that the present invention provides for a compound of the formula

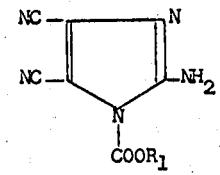

wherein $R_1$ is selected from the group consisting of straight or branched chain alkyl of 1 to 12 carbon atoms, alkenyl of 3 to 4 carbon atoms, propargyl, methoxyethyl, alkyl of 2 to 4 carbon atoms substituted with one or two chlorine or bromine atoms and cyclohexyl. Within this group the invention also provides for compounds in which $R_1$ is alkyl of 4 to 5 carbon atoms. Compounds in which $R_1$ is straight or branched chain alkyl of 1 to 12 carbon atoms, lower alkenyl or lower alkynyl are also provided for in the present invention.

What is claimed is:

1. A compound of the formula

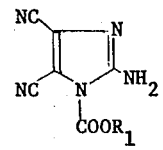

wherein $R_1$ is selected from the group consisting of
straight or branched chain alkyl of 1 to 12 carbon atoms,
alkenyl of 3 to 4 carbon atoms, propargyl, methoxyethyl,
alkyl of 2 to 4 carbon atoms substituted with one or two chlorine or bromine atoms and cyclohexyl.

2. A compound of the formula

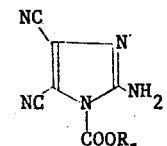

wherein $R_1$ is selected from the group consisting of straight or branched chain alkyl of 1 to 12 carbon atoms, lower alkenyl and lower alkynyl.

3. A compound of the formula

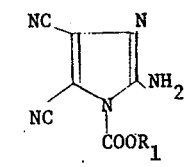

wherein $R_1$ is alkyl of 4 to 5 carbon atoms.

4. 2-amino-1-n-butoxycarbonyl-4,5-dicyanoimidazole 5. 2-amino-4,5-dicyano-1-n-pentyloxycarbonylimidazole 6. A fungicidal composition for plants comprising an inert carrier and a fungicidally effective amount of the compound of claim 1.

7. A fungicidal composition for plants comprising an inert carrier and a fungicidally effective amount of the compound of claim 2.

8. A fungicidal composition for plants comprising an inert carrier and a fungicidally effective amount of the compound of claim 3.

9. A fungicidal composition for plants comprising an inert carrier and a fungicidally effective amount of the compound of claim 4.

10. A fungicidal composition for plants comprising an inert carrier and a fungicidally effective amount of the compound of claim 5.

11. A method of preventing injury to plants due to fungi comprising applying to the locus to be protected an effective amount of the compound of claim 1.

12. A method of preventing injury to plants due to fungi comprising applying to the locus to be protected an effective amount of the compound of claim 2.

13. A method of preventing injury to plants due to fungi comprising applying to the locus to be protected an effective amount of the compound of claim 3.

14. A method of preventing injury to plants due to fungi comprising applying to the locus to be protected an effective amount of the compound of claim 4.

15. A method of preventing injury to plants due to fungi comprising applying to the locus to be protected an effective amoutn of the compound of claim 5.

* * * * *

UNITED STATES PATENT OFFICE
CERTIFICATE OF CORRECTION

Patent No. 3,983,241          Dated September 28, 1976

Inventor(s) Sho Hashimoto et al

It is certified that error appears in the above-identified patent and that said Letters Patent are hereby corrected as shown below:

On the Title Page, Item [73] should read:
--- Nippon Soda Company, Limited Shin-Ohtemachi Building Ohtemachi, Chiyoda-ku Tokyo, Japan ---.

Signed and Sealed this

Eighteenth Day of January 1977

[SEAL]

Attest:

RUTH C. MASON  
*Attesting Officer*

C. MARSHALL DANN  
*Commissioner of Patents and Trademarks*